United States Patent [19]

Bhatnagar et al.

[11] Patent Number: 6,054,465
[45] Date of Patent: Apr. 25, 2000

[54] HEMOREGULATORY COMPOUNDS

[75] Inventors: Pradip Kumar Bhatnagar, Exton; Dirk Andries Heerding, Malvern, both of Pa.

[73] Assignee: SmithKline Beecham Corporation, Philadelphia, Pa.

[21] Appl. No.: 09/068,493

[22] PCT Filed: Nov. 12, 1996

[86] PCT No.: PCT/US96/18343

§ 371 Date: May 12, 1998

§ 102(e) Date: May 12, 1998

[87] PCT Pub. No.: WO97/18210

PCT Pub. Date: May 22, 1997

Related U.S. Application Data

[60] Provisional application No. 60/006,570, Nov. 13, 1995.

[51] Int. Cl.[7] .......................... A61K 31/44; A61K 31/495; C07D 221/02; C07D 241/02; C07D 209/02
[52] U.S. Cl. .......................... 514/300; 546/112; 546/124; 546/132; 544/406; 548/452; 514/299; 514/255
[58] Field of Search .................... 546/112, 124, 546/132; 544/406; 514/299, 255, 300; 548/452

[56] References Cited

U.S. PATENT DOCUMENTS

| | | | |
|---|---|---|---|
| 2,678,317 | 5/1954 | Payne et al. | 546/124 |
| 2,798,874 | 7/1957 | Archer et al. | 546/124 |
| 2,845,427 | 7/1958 | Archer et al. | 546/124 |
| 5,498,614 | 3/1996 | Desai et al. | 514/299 |
| 5,723,472 | 3/1998 | Myazawa et al. | 514/294 |
| 5,753,673 | 5/1998 | Ohuchi et al. | 514/304 |

OTHER PUBLICATIONS

Veenstra,Siem J ,Studies on the active conformation of NK1 antagonist. CA 126:233088v, 1997.

Ohuchi Yutaka, Prep. of quinolinecarboxylic acid . . . , CA 124:202043f, Nov. 1995.

Patel Alain, Cinnamic Acid Derv, and their therapeutic use. CA 103:37214, Apr. 1985.

*Primary Examiner*—Alan L. Rotman
*Assistant Examiner*—Rita Desai
*Attorney, Agent, or Firm*—Linda E. Hall; Stephen A. Venetianer; Charles M. Kinzig

[57] ABSTRACT

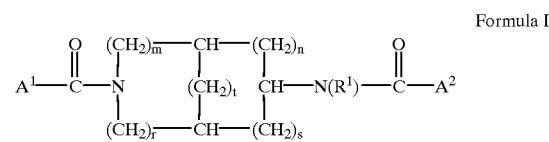

Formula I

The present invention relates to novel compounds of the Formula I which have hemoregulatory activities and can be used to stimulate hematopoiesis and for the treatment of viral fungal and bacterial infectious diseases.

8 Claims, No Drawings

HEMOREGULATORY COMPOUNDS

This is a 371 application of PCT/US96/18343, filed Nov. 12, 1996, which claims the benefit of priority of Provisional Application Ser. No. 60/006,570, filed Nov. 13, 1995.

FIELD OF THE INVENTION

The present invention relates to novel compounds which have hemoregulatory activities and can be used to stimulate hematopoiesis and for the treatment of viral, fungal and bacterial infectious diseases.

BACKGROUND OF THE INVENTION

The hematopoietic system is a life-long cell renewal process whereby a defined stem cell population gives rise to a larger population of mature, differentiated blood cells (Dexter T M. Stem cells in normal growth and disease. Br Med J 1987; 195:1192–1194) of at least nine different cell lineages (erythrocytes, platelets, eosinophils, basophils, neutrophils, monocytes/macrophages, osteoclasts, and lymphocytes) (Metcalf D. The Molecular Control of Blood Cells. 1988; Harvard University Press, Cambridge, Mass.). Stem cells are also ultimately responsible for regenerating bone marrow following treatment with cytotoxic agents or following bone marrow transplantation.

The major dose-limiting toxicities of most standard antineoplastic drugs are related to bone marrow suppression, which if severe and prolonged, can give rise to life-threatening infectious and hemorrhagic complications. Myelosuppression is predictable and has been reported to be dose-limiting in greater than 50% of single-agent Phase I trials cytotoxic compounds (Merrouche Y, Catimel G, Clavel M. Hematopoietic growth factors and chemoprotectants; should we move toward a two-step process for phase I clinical trials in oncology? Ann Oncol 1993; 4:471–474). The risk of infection is directly related to the degree of myelosuppression as measured by the severity and duration of neutropenia (Brody G P, Buckley M, Sathe Y S, Freireich E J. Quantitative relationship between circulating leukocytes and infections with acute leukemia Ann In Med 1965; 64:328–334).

The control of hematopoiesis involves the interplay of a variety of cytokines and growth factors during various stages of the hematopoietic cascade, including early pluripotent stem cells and mature circulating effector cells. These regulatory molecules include granulocyte colony stimulating factor (G-CSF), granulocyte-macrophage stimulating factor (GM-CSF), macrophage-colony stimulating factor (M-CSF), and a variety of interleukins which have overlapping, additive and synergistic actions which play major roles in host defence. Mechanistically, this is accomplished by enhancing the production of granulocytes and macrophages, as well as by the activation of effector cell functions (Moore M A S. Hemopoietic growth factor interactions: in vitro and in vivo preclinical evaluation. Cancer Surveys 1990; 9:7–80). These coordinated activities support optimal host defences which are necessary for fighting bacterial, viral and fungal infections.

Strategies to prevent or reduce the severity of neutropenia and myelotoxicity include the use of hematopoietic growth factors and/or other hematopoietic cytokines. Such treatments are becoming common practice, in that they offer the potential of increased doses of cytotoxic agents that may improve the therapeutic efficacy of antineoplastic agents, and reduce the morbidity associated with their use (Steward W P. Granulocyte and granulocyte-macrophage colony stimulating factors, Lancet 1993; 342:153–157). Clinical studies have demonstrated the G-, GM- and/or M-CSF may reduce the duration of neutropenia, accelerate myeloid recovery, and reduce neutropenia-associated infections and other infectious complications in patients with malignancies who are receiving cytotoxic chemotherapy or in high infectious-risk patients following bone marrow transplantation (Steward W P. Granulocyte and granulocyte-macrophage colony stimulating factors, Lancet 1993; 342:153–157 and Munn D H, Cheung N K V. Preclinical and clinical studies of macrophage colong-stimulating factor. Semin Oncol 1992; 19:395–407).

Synthetic peptides have been reported to induce the synthesis and release of haematoporetic mediators, including m-CSF from bone marrow stromal elements see U.S. patent application Ser. No. 08/001,905.

We have now found certain novel non-peptide compounds which have a stimulative effect on myelopoietic cells. They are useful in stimulating myelopoiesis in patients suffering from reduced myelopoietic activity, including bone marrow damage, agranulocytosis and aplastic anemia including patients having depressed bone marrow function due to immunosuppressive treatment to suppress tissue reactions i.e. in bone marrow transplant surgery. They may also be used to promote more rapid regeneration of bone marrow after cytostatic chemotherapy and radiation therapy for neoplastic and viral diseases. They may be of particular value where patients have serious infections due to a lack of immune response following bone marrow failure. They are useful in the treatment and prevention of viral, fungal and bacterial disease.

SUMMARY OF THE INVENTION

This invention comprises compounds, hereinafter represented as Formula (I), which have hemoregulatory activities and can be used to stimulate hematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The compounds are also useful in the treatment and prevention of viral, fungal and bacterial infectious diseases, particularly Candida and Herpes in both immunosuppressed and "normal" subjects. They are useful in the treatment of sepsis caused by gram negative and gram positive organisms.

These compounds may also be used in combination with the myelosuppresive agents of co-pending U.S. Application Ser. No. 07/799,465 and U.S. Pat. No. 4,499,081, incorporated by reference herein, to provide alternating peaks of high and low activity in bone marrow cells, thus augmenting the natural circadian rhythm of hematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of Formula (I) and a pharmaceutically acceptable carrier.

This invention further constitutes a method for stimulating the myclopoietic system of an animal, including humans, which comprises administering to an animal in need thereof, an effective amount of a compound of Formula (I).

This invention also constitutes a method for preventing and treating viral, fungal and bacterial infections including sepsis, in immunosuppressed and normal animals, including humans, which comprises administering to an animal in need thereof, an effective amount of a compound of Formula (I).

DETAILED DESCRIPTION OF THE INVENTION

The compounds of the invention are represented by structural Formula I $$A^1-\underset{O}{\overset{O}{C}}-N\begin{matrix}(CH_2)_m-CH-(CH_2)_n\\(CH_2)_t\phantom{-}CH-N(R^1)\\(CH_2)_r-CH-(CH_2)_s\end{matrix}-\underset{O}{\overset{O}{C}}-A^2 \quad (I)$$

$A^1$ and $A^2$ are independently $Z-(CH_2)_k-(NR^2)_y-$;

Z is independently a 4–10 membered mono- or bicyclic heterocyclic ring system containing up to four heteroatoms N, O, S in the ring in which at least one heteroatom is N, and wherein the ring is substituted or unsubstituted by one or two $C_{1-4}$alkyl, F, Cl, Br, I, $C_{1-4}$ alkoxy, $(CH_2)_mR_4$, oxo, oxime, $O-C_{1-4}$alkyloxime, hydroxy, $N(R_3)_2$, acylamino or aminoacyl groups, 8, 9, 10 membered monocyclic ring systems being excluded;

$R^1$ and $R^2$ are independently hydrogen, $C_{1-4}$alkylC(O)R_4, $C_{1-4}$alkyl or R1 and R_2 are benzyl which is optionally substituted by one or two $C_{1-4}$alkyl, $C_{1-4}$alkoxy, F, Cl, I, Br, OH, or $N(R_3)_2$;

$R_3$ is independently hydrogen, $C_{1-4}$alkyl, or benzyl;

$R_4$ is independently $OR_3$, $N(R_3)_2$ or $SR_3$; and k is an integer from 0 to 4;

m is an integer from 0 to 2;

n is an integer from 0 to 2;

r is 1 or 2;

s is 1 or 2;

t is an integer from 0 to 2;

y is zero or one;

or a pharmaceutically acceptable salt thereof;

provided:
  a) when t is 0, m, n, r and s are not all 2;
  b) when t is 1 or 2, m+r is one or two and n+s is one or two.
  c) when m and n are 0 and s is 1 t is 1 or 2.

$C_{1-4}$alkyl groups may be straight or branched.

The compounds of the present inventiion may contain one or more asymmetric carbon atoms and may exist in racemic and optically active form. All these compounds and diastereomers are contemplated to be within the scope of the present invention.

Z in the above Formula (I) denotes an optionally substituted pyrrolyl, isopyrrolyl, pyrazolyl, isoimidazolyl, triazolyl, iosxazolyl, oxazolyl, thiazolyl, isothiazolyl, oxadiazolyl, pyridinyl, pyridazinyl, pyrimidinyl, pyrazinyl, pyrrolidinyl, piperazinyl, triazinyl, morpholinyl, indolyl, indoleninyl, isobenzazolyl, pyrindinyl, ioindazolyl, indoxazinyl, benzoxazolyl, quinolinyl, isoquinolinyl, cinnolinyl, quinazolinyl, naphthyridinyl, pyridopyridinyl, tetrahydroquinolinyl, tetrahydroisoquinolinyl, quinoxalinyl, indolinyl, pyrrolidonyl, imidazolyl, imidazolidinyl, imidazolinyl, piperidyl, tetrazolyl, quinuclidinyl, azetidinyl, or purinyl;

Preferred compounds are those wherein Z is optionally substituted pyridinyl, pyrimidinyl, pyrazinyl, pyridazinyl, quinolinyl, tetrahydroquinolinyl, azetidinyl, or pyrrolidinyl;

More preferred compounds are those wherein Z is optionally substituted 2-pyridinyl, 2-pyrimidinyl, 2-pyrazinyl, 2-pyrrolidon-5-yl, or pyrrolidinyl.

Preferred compounds are N,N-Bis(picolinoyl)-3-aminopyrrolidine, N,N-Bis(picolinoyl)-4-aminopiperidine and N,N-Bis(picolinoyl)-4-aminoperhydroazepine.

Preferred compounds are N,N'-bis(picolinoyl)-3-amino-8-azabicyclo[3.2.1]octane or N,N'-bis(pyroglutamoyl)-3-amino-8-azabicyclo[3.2.1]octane.

METHODS OF PREPARATION

Compounds of Formula (I) wherein $A^1, A^2$, m, n, r, s, t and $R^1$ are defined as in Formula (I) are prepared by methods analogous to those described in Scheme 1. Appropriate diamines (such as 1 in Scheme 2) are bis-acylated with a suitable heterocyclic acid (such as 2 in Scheme 1) using an activating agent (such as BOP reagent) with a suitable base (such as iPr_2NEt) in a polar aprotic solvent (such as DMF) to give the final product.

Scheme 1 a) BOP, HOBt, iPr_2NEt, DMF

In order to use a compound of the Formula (I) or a pharmaceutically acceptable salt thereof for the treatment of humans and other mammals it is normally formulated in accordance with standard pharmaceutical practice as a pharmaceutical composition.

According to a still further feature of the present invention there are provided pharmaceutical compositions comprising as active ingredient one or more compounds of Formula (I) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the compounds of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the compounds of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.05–50 mg, for example 0.05–5 mg of the compound of formula (I) or salt thereof.

According to a still further feature of the present invention there is provided a method of stimulation of myelopoiesis which comprises administering an effective amount of a pharmaceutical composition as hereinbefore defined to a subject.

No unacceptable toxicological effects are expected when compounds of the invention are administered in accordance with the present invention.

The biological activity of the compounds of Formula (I) are demonstrated by the following tests.

Induction of Hematopoietic Synergistic Activity in Stromal Cells

The murine bone marrow derived stromal cell line, C6.4 is grown in 12 well plates in RPMI 1640 with 10% FBS. Upon reaching confluence, the C6.4 cells are washed and the media exchanged with fresh RPMI 1640 without FBS. Confluent cell layers of murine C6.4 cells are treated with compound. Cell-free supernatants are collected 18 hours later. Supernatants are fractionated with a Centricon-30 molecular weight cut-off membrane. C6.4 cell hematopoietic synergistic factor (HSF) activity is measured in a murine CFU-C assay.

CFU-C Assay

Bone marrow cells are obtained from C57B1/6 female mice and suspended in RPMI 1640 with 10% FBS. Bone marrow cells (7.5E+4 cells/mL) are cultured with sub optimal levels of CFU plus dilutions of test C6.4 cell 30K-E supernatants from above in a standard murine soft agar CFU-C assay. Cell aggregates >50 cells are counted as colonies. The number of agar colonies counted is proportional to the amount of HSF present within the C6.4 bone marrow stromal line supernatant.

Effector Cell Function Assay

Female C57B1 mice are administered test compound IP or PO daily for 8 days. Resident peritoneal exudate cells (PEC) utilized ex vivo from treated or untreated mice are harvested with cold calcium and magnesium-free DPBS supplemented with heparin and antibiotics within 2–4 hours following the last injection. Adherent PEM populations are prepared by incubating standardized PEC suspensions in microtiter dishes for 2 hours at 37° C. (5% $CO_2$) and removing nonadherent cells by washing the wells with warm buffer.

The superoxide dismutase-inhibitable (SOD) superoxide released by effector cells in response to a in vitro stimulation by phorbol myristate acetate (PMA) (100–200 nM) or pre-opsonized (autologous sera) live C. albicans (E:T=1:10) are quantitated in a microtiter ferricytochrome c reduction assay. The assay is performed in the presence of 1% gelatin/H SS and 8OuM ferricytochrome c in a total volume of 200 uL/well. The nmoles of cytochrome c reduced/well is calculated from spectrophotometric readings (550 nm) taken following a 1 hour incubation at 37° C. (5% $CO_2$). The amount of SOD-inhibitable cytochrome c reduced is determined by the inclusion of wells containing SOD (200 U/well). Baseline superoxide release is determined in the absence of stimuli. Experimental data are expressed as a percentage of the control group.

The following examples are illustrative and are not limiting of the compounds of this invention.

EXAMPLE 1

N,N'-Bis(picolinoyl)-3-amino-8-azabicyclo[3.2.1] octane

3-Amino-8-azabicyclo[3.2.1]octane (one molar equivalent) is dissolved in DMF. Picolinic acid (3 molar equivalents), BOP reagent (3 molar equivalents), HOBt hydrate (3 molar equivalents) and iPr$_2$NEt (5 molar equivalents) are added sequentially. The reaction is stirred at room temeprature for 18 h and then it is poured into brine. The aqueous phase is extracted with EtOAc and the combined organic phases are washed with water. The organic phase is dried over $Na_2SO_4$ and the solvent is removed to give the title compound.

EXAMPLE 2

N,N'-Bis(pyroglutamoyl)-3-amino-8-azabicyclo [3.2.1]octane

In a manner analogous to Example 1,3-amino-8-azabicyclo[3.2.1]octane (one molar equivalent), picolinic acid (3 molar equivalents), BOP reagent (3 molar equivalents), HOBt hydrate (3 molar equivalents) and iPr$_2$NEt (5 molar equivalents) in DMF give the title compound.

EXAMPLE 3

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form.I) | 0.5 mg |
| 2. Corn Starch | 20 mg |
| 3. Alginic acid | 20 mg |
| 4. Sodium alginate | 20 mg |
| 5. Mg stearate | 1.3 mg |

Procedure for tablets:
Step 1 Blend ingredients No. 1, No. 2, No. 3 and No. 4 in a suitable mixer/blender.
Step 2 Add sufficient water portion-wise to the blend from Step 1 with careful mixing after each addition. Such additions of water and mixing until the mass is of a consistency to permit its converion to wet granules.
Step 3 The wet mass is converted to granules by passing it through an oscillating granulator using a No. 8 mesh (2.38 mm) screen.
Step 4 The wet granules are then dried in an oven at 140° F. (60° C.) until dry.
Step 5 The dry granules are lubricated with ingredient No. 5.
Step 6 The lubricated granules are compressed on a suitable tablet press.

Parenteral Formulation

A pharmaceutical composition for parenteral administration is prepared by dissolving an appropriate amount of a compound of Formula I in polyethylene glycol with heating. This solution is then diluted with water for injections Ph Eur. (to 100 ml). The solution is then sterilized by filtration through a 0.22 micron membrane filter and sealed in sterile containers.

We claim:

1. A compound of Formula (I)

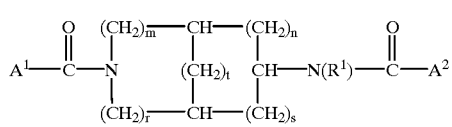

$A^1$ and $A^2$ are independently $Z-(CH_2)_k-(NR^2)_y-$;

Z is independently a pyridinyl, pyrimidinyl, pyrazinyl, pyridazinyl, or pyrrolidonyl N, and wherein the ring is substituted or unsubstituted by one or two $C_{1-4}$alkyl, F, Cl, Br, I, $C_{1-4}$ alkoxy, $(CH_2)_m R_4$, oxo, oxime, $O-C_{1-4}$alkyloxime, hydroxy, $N(R_3)_2$, acylamino or aminoacyl groups, 8, 9, 10 membered monocyclic ring systems being excluded;

$R^1$ and $R^2$ are independently hydrogen, $C_{1-4}$alkylC(O)R$_4$, $C_{1-4}$alkyl or R1 and R$_2$ are benzyl which is optionally substituted by one or two $C_{1-4}$alkyl, $C_{1-4}$alkoxy, F, Cl, I, Br, OH, or $N(R_3)_2$;

$R_3$ is independently hydrogen, $C_{1-4}$alkyl, or benzyl;

$R_4$ is independently $OR_3$, $N(R_3)_2$ or $SR_3$; and k is an integer from 0 to 4;

m is an integer from 0 to 2;

n is an integer from 0 to 2;

r is 1 or 2;

s is 1 or 2;

t is an integer from 0 to 2;

y is zero or one;

or a pharmaceutically acceptable salt thereof;

provided:
a) when t is 0, m, n, r and s are not all 2;
b) when t is 1 or 2, m+r is one or two and n+s is one or two.
c) when m and n are 0 and s is 1 t is 1 or 2.

2. A compound of claim 1 wherein Z is optionally substituted pyridinyl, pyrimidinyl, pyrazinyl, pyridazinyl, or pyrrolidonyl.

3. A compound of claim 2 wherein Z is optionally substituted 2-pyridinyl, 2-pyrimidinyl, 2-pyrazinyl, 2-pyrrolidon-5-yl, or 2-pyrrolidinyl.

4. A compound of claim 1 selected from N,N'-bis (picolinoyl)-3-amino-8-azabicyclo[3.2.1]octane or N,N'-bis (pyroglutamoyl)-3-amino-8-azabicyclo[3.2.1]octane.

5. A pharmaceutical composition comprising an effective amount of a compound of Formula (I) and a pharmaceutical carrier or excipient.

6. A method of treating a susceptible or bacterial infections which comprises administering to a human or other mammal in need thereof, an effective amount of a compound of Formula I.

7. A method of stimulating mylopoiesis in a human or other mammal in need thereof by administering a compound of claim 1.

8. A method of treating sepsis in a human or other mammal in need thereof by administering a compound of claim 1.

* * * * *